United States Patent [19]

Wolfbeis et al.

[11] Patent Number: 5,340,722
[45] Date of Patent: Aug. 23, 1994

[54] METHOD FOR THE DETERMINATION OF THE CONCENTRATION OF AN ENZYME SUBSTRATE AND A SENSOR FOR CARRYING OUT THE METHOD

[75] Inventors: Otto S. Wolfbeis, Graz; Wolfgang Trettnak, Mooskirchen, both of Austria

[73] Assignee: AVL Medical Instruments AG, Schauffhausen, Switzerland

[21] Appl. No.: 38,065

[22] Filed: Mar. 29, 1993

Related U.S. Application Data

[63] Continuation of Ser. No. 857,114, Mar. 20, 1992, abandoned, which is a continuation of Ser. No. 395,463, Aug. 18, 1989, abandoned.

[30] Foreign Application Priority Data

Aug. 24, 1988 [AT] Austria .................... A 2093/88

[51] Int. Cl.$^5$ .................. C12Q 1/54; C12Q 1/26; C12Q 1/32; C12Q 1/28
[52] U.S. Cl. .................. 435/14; 435/25; 435/26; 435/28
[58] Field of Search ............ 435/25, 28, 14, 26

[56] References Cited

U.S. PATENT DOCUMENTS

| | | |
|---|---|---|
| 4,344,388 | 8/1988 | Schultz . |
| 4,758,323 | 7/1988 | Davis et al. ............ 204/403 |
| 4,803,049 | 2/1989 | Hirschfeld et al. ........ 422/58 |
| 4,806,415 | 2/1989 | Fossati ................. 435/14 |
| 4,830,959 | 5/1989 | McNeil et al. ............ 435/7 |

OTHER PUBLICATIONS

Lehninger 1970 Biochemistry pp. 372–374 Worth Publishers, N.Y.
Stryer, (1981) Biochemistry 2d edition, WH Freeman & Co. San Francisco, pp. 287–288.
Trenttnak et al. (1989) Analyt Chim. Acta 221:195–203.
Goldfinch et al., "Solid–Phase Optoelectronic Sensors in Biochemical Analysis" in *Analytical Biochemistry* 138, 430–436 (1984).
Chemical Abstracts, vol. 95, p. 397 (1981) 95:765093.
Wangsa et al., "Fiber-Optic Biosensors Based on the Fluorometric Detection of Reduced Nicotinanmide Adenine Dinucleotide" in *Anal. Chem.* 60, 1080 (1988).

*Primary Examiner*—Esther L. Kepplinger
*Assistant Examiner*—David R. Preston
*Attorney, Agent, or Firm*—Watson, Cole, Grindle & Watson

[57] ABSTRACT

A method for the continuous and reversible determination of the concentration of an enzyme substrate such as glucose in an specimen, wherein the specimen is brought into contact with a corresponding enzyme selected from oxidases and oxygenases and to which a flavin coenzyme (FMN, FAD) is bonded, the flavin coenzyme changing to a reduced form by the enzyme substrate and to an oxidized form by molecular oxygen dissolved in the specimen, and the change in the fluorescence spectrum, produced by means of the reduction of the flavin coenzyme, is measured.

8 Claims, 4 Drawing Sheets

METHOD FOR THE DETERMINATION OF THE CONCENTRATION OF AN ENZYME SUBSTRATE AND A SENSOR FOR CARRYING OUT THE METHOD

CROSS-REFERENCE TO RELATED APPLICATIONS

This application is a continuation of application Ser. No. 857,114, filed Mar. 20, 1992, now abandoned, which was a continuation of application Ser. No. 395,463, filed Aug. 18, 1989, now abandoned.

BACKGROUND OF THE INVENTION

The invention relates to a process for determining the concentration of an enzyme substrate in a specimen, wherein the specimen is brought into contact with a corresponding enzyme and its fluorescent spectrum is measured according to the fluorescent excitation and a change in the fluorescent spectrum is used as a measure for the change in the concentration of the enzyme substrate. The invention also relates to an optical sensor used in the process.

The determination of enzyme substrates, for example glucose, plays an important role in the clinical diagnosis, since it permits a comprehensive statement concerning presence of metabolic disorders (e.g. diabetes mellitus). Moreover, glucose is also frequently determined within the framework of the quality controls of the food industry and in biotechnology as well, since the current bioreactors demand a continuous supply of nutrients, especially glucose. Glucose and other sensors for enzyme substrates play an important role because a continuous and reversible sensing of the enzyme substrate concentrations is desired. For example, a reliable glucose sensor is currently still the limiting factor in the development of an artificial pancreas.

A plurality of determination methods in this context are already known. A distinction is made between continuous and discontinuous processes. The discontinuous processes have the drawback that they must be carried out by destroying the specimen and they require experimental conditions which, for example, are unsuitable for in-vivo applications (addition of aggressive reagents, work in the presence of strong acids and alkaline solutions). Another drawback of the discontinuous method is that to obtain a continuous monitoring it is necessary to sample continuously in correspondingly short time intervals. For this reason priority has recently been given to the development of continuous sensors for glucose. A distinction is made between two large groups, viz. the electrochemical and the optic biosensors for glucose.

An overview of the prior art can be found in "Biosensors: Fundamentals and Applications," Oxford University Press, Oxford (1987) by H. P. F. Turner, I. Karube and G. Wilson. It is clear from this text that the electrochemical sensors for glucose (and other clinically relevant enzyme substrates) have reached a high state of the art. Of course, electrochemical biosensors suffer from various drawbacks. One of the biggest problems with electrochemical sensors is that the mandatory electrolyte bridge is quite susceptible, and gives occasion to, continuous drift. Moreover, electrochemical sensors can be operated only for short distances, because they produce an electric connection to the test chamber, a state that also presents a specific risk, especially in in-vivo studies. In the case of bioreactors one drawback is that electrochemical sensors can be only slightly sterilized.

Recently alternatives to electrochemical sensors have been sought and they have been found in optical sensors, in particular in fiber optical sensors. In contrast to electrochemical sensors, optical sensors require no reference electrode, permit the transport of light over great distances and form no electrical connection to the test object so that they are also not influenced by static potentials or body potentials. In the known optical biosensors for glucose and similar enzymatic, degradable substrates two types can be distinguished.

In the first type the enzymatic reaction can run its course while the one species is being formed that can be detected with a transducer element. For example, the oxidation of glucose by means of the enzyme glucose oxidase (GOD) proceeds according to the following chemical reaction:

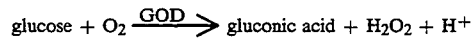

Thus it is possible, through the measurement of the consumption of oxygen or the formation of $H_2O_2$ or the drop in the pH value, to deduce the glucose concentration that is present, since all of these parameters change parallel to the change in the glucose concentration. An optical arrangement to measure the glucose, which is based on the determination of the consumed oxygen, is described in Adv. Exp. Med. Biol. 75, 65 (1976) or in the DE-PS 2,948,904. A glucose sensor, which is based on the measurement of the acid formed ($H^+$) by pursuing the change in color of an added pH indicator, is described in Analytical Biochem. 138, 450 (1984). A continuous sensor for glucose, which is based on the measurement of $H_2O_2$ formed, has not been disclosed to date.

Another principle for determining the glucose concentration is described in an affinity sensor of U.S. Pat. No. 4,344,438. It is an optical sensor for all kinds of plasma components which are in a position to enter into a competitive binding on a receptor side in a measuring chamber on the end of a light guide. The competitive ligand is labelled with fluorescent light and is forced into this chamber depending on the quantity of ligands, whereupon the absorbed or emitted light is seen by the light guide. A typical example is one in which concanavalin A is immobilized on sepharose and fluorescein labelled dextran is bonded on the concanavalin. Glucose is in a position to displace the labelled dextran, whereupon the fluorescence labelled dextran is seen by the light guide, and the result is that an increase in the intensity of fluorescence is observed.

A process of the aforementioned kind is described in Anal. Chem. 60, 1080 (1988) by Wangsa and Arnold, and in particular for the determination of lactate. Lactate is converted into pyruvate by means of the enzyme lactate dehydrogenase; at the same time the non-bonded $NAD^+$ of the enzyme is converted into the highly fluorescing NADH. The concentration of lactate present is deduced from measuring the increase in the fluorescence of NADH. Of course, the sensor suffers from various drawbacks. The greatest drawback is that it is not reversible, since the reaction terminates when all $NAD^+$ is consumed. For this reason, fresh $NAD^+$ must be constantly added to the reaction. This is a general drawback of all biosensors, which are based on the measurement of the intrinsic fluorescence of NADH. Thus it is not a sensor in the restricted meaning since it does not fulfill the condition of a complete reversibility.

The ultraviolet wavelengths of 350 nm that are necessary for the fluorescence excitation of NADH can be regarded as another drawback since not only the glass fibers but also the plastic fibers do not guide or guide only slightly this light and the requisite light sources are also relatively expensive.

All of the aforementioned processes or sensors have the drawback that they are either irreversible or require a relatively complex sensor structure, in essence have an enzymatically active layer and also a transducer element such as an oxygen or pH optode, or, as in the case of the glucose sensor based on the competitive binding, need a small but relatively complicated measuring chamber with several kinds of immobilization steps.

The object of the invention is to propose a simple process to determine the concentrations of an enzyme substrate in a specimen and an optical sensor as well to carry out this process, wherein, in particular, there is a reversible sensor for continuous glucose determination.

The problem is solved by the invention in that for the continuous, reversible determination of the concentration of the enzyme substrate, an enzyme, selected from the group of oxidases and oxygenases, is used with a flavin coenzyme (FMN, FAD), which is bonded thereto and which is brought into the reduced form by means of the enzyme substrate and is brought into the oxidized form by means molecular oxygen dissolved in the specimen, wherein the change in the intrinsic fluorescence of the flavin coenzyme, produced by means of the reduction of the flavin coenzyme, is measured.

The process of the invention is based on the surprising observation that the intrinsic fluorescence of the enzymes, which have as their cofactor a coenzyme selected from the group of flavins, changes during the enzymatic activity in a characteristic manner and, in particular, contrary to the prevailing teachings, according to which GOD is not supposed to fluoresce and/or the fluorescence of FAD in the enzyme is supposed to be quenched by means of the protein. In the process of the invention, the intensity of the fluorescence can increase or decrease. This change in fluorescence is completely reversible in the presence of oxygen and can thus be used as the direct optical information for an optical biosensor. The use of a transducer element such as an oxygen or pH sensor is, therefore, no longer necessary. Furthermore, the wavelengths of excitation of flavoproteins is in a spectral range of usually 400 to 500 nm and are, therefore, suitable for use in current glass or plastic light guides. Also, when the emission of wavelengths exceeds 500 nm, a large Stokes' displacement is given, so that the optical separation of excitation and fluorescence radiation is simple.

It is known that for flavo enzymes the redox reaction runs its course at a flavin coenzyme. Flavin coenzymes are such coenzymes, which have a flavin mononucleotide (FMN) or a flavin adenine dinucleotide (FAD).

During enzymatic oxidation the cofactor simultaneously transforms into a reduced form, which is then immediately reconverted into the oxidized form by means of oxygen (as the second substrate). The transition from oxidized form to reduced form is linked to a change in the fluorescence properties, which serve as the analytic information.

One embodiment of the invention provides that a glucose oxidase is used with a flavin adenine dinucleotide (FAD) to determine the glucose concentration. The following two equations reflect the two step reaction scheme:

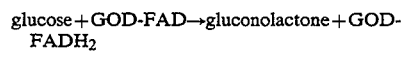

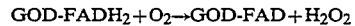

According to the invention it is also possible to determine with a flavin coenzyme the alcohol or glutamic acid concentration with the aid of the enzyme, alcohol oxidase or glutamic acid oxidase.

The process of the invention can be applied to all enzymatic reactions in which FMN or FAD occur as the coenzyme and oxygen is present in the specimen. FMN and FAD are present preferably in enzymes selected the group of oxidases and oxygenases. Typical examples of such enzymes (with enzyme classification) are:

Glucose oxidase (EC 1.1.3.4), galactose oxidase (EC 1.1.3.9), lactate oxidase (EC 1.1.3.2), lactate monooxygenase (EC 1.13.12.4), xanthine oxidase (EC 1.2.3.2), aspartate oxidase (EC 1.4.3.1), L-amino acid oxidase (EC 1.4.3.2), bilirubin oxidase (EC 1.3.3.5), cholesterol oxidase (EC 1.1.3.6), monoamine oxidase (EC 1.4.3.4), thiamine oxidase (EC 1.4.3.6), urate oxidase (EC 1.7.3.3), sulfite oxidase (EC 1.8.3.1), cytochrome oxidase (EC 1.9.3.1), lipoxygenase (EC 1.13.1.13), alcohol oxidase (EC 1.1.3.13) and various other enzymes of this kind.

If the intensity of fluorescence is plotted as a function of the concentration of the enzyme substrate (see also FIG. 5), a region is found in which small increases in concentration lead to a large increase in the intensity of fluorescence. Thus, the sensor is very sensitive in this range. According to the invention, a provision can also be made here that, before the specimen is measured, molecular oxygen in known concentration is added to the specimen so that that region of the response function in which small variations in the concentration of the enzyme substrate lead to large changes in the intensity of fluorescence, is displaced into a pre-set range of concentration. This process can be applied, for example in bioreactors, where precise measurements are mandatory in specific ranges of concentration.

Another possibility to control the range of sensitivity of the process is to install a so-called diffusion threshold before the sensor material. The result is that a much smaller concentration of substrate prevails in the interior of the sensor than on the outside. Thus, it is possible to expand the favorable region of the response curve for the measurement.

According to the invention, an optical sensor to determine the concentration of an enzyme substrate with a carrier element which is permeable to the excitation and fluorescent light and on which a sensor layer is immobilized on the specimen side, has the characteristic that the sensor layer has an enzyme selected from the group of oxidases and oxygenases with a flavin coenzyme bonded thereto.

The optical sensor is conceivable in different embodiments. Thus, according to the invention, the enzyme can be present in an enzyme gel or an enzyme solution, which is mechanically immobilized by means of a membrane whose exclusion molecular weight is less than 30,000 at the carrier element, for example, a planar carrier. The mechanical immobilization can occur, for example, due to the fact that the enzyme is held back with the aid of a cellulose membrane whose exclusion molecular weight is below 30,000, since most of the enzymes have molecular weights exceeding 60,000.

Another embodiment of the invention provides that the enzyme is present in a sensor layer comprising hydrogel or polyacrylamide. In this manner the enzyme is physically immobilized by embedding in a gel.

Furthermore, it is provided that the enzyme is bonded directly to the surface of the carrier element by means of chemical immobilization. The chemical immobilization can occur either in an electrostatic manner, e.g., by bonding to an ion immersion membrane or by covalent bonding to a material such as cross-linked serum albumin or to a membrane such as cellulose or polyamide.

In this manner the FMN or FAD containing enzyme is applied to a fixed carrier element or mechanically, physically or chemically immobilized on its surface. The enzyme layer faces the specimen and the fluorescence radiation is excited or absorbed from the rear of the fixed and optically transparent carrier element. In order to prevent interferences by means of the intrinsic fluorescence of the test medium, it can be provided that the enzymatic sensor layer is covered on the surface with an optically non-transparent medium, which is, however, permeable to the substrate to be determined. Such materials are, e.g., hydrogels dyed dark with active carbon. In the case of various volatile enzyme substrates such as alcohol it is also possible to cover with a hydrophobic layer such as black teflon or silicon.

Finally the invention provides that the enzyme is immobilized directly on the end of the light guide.

The invention is explained in detail with reference to the drawings as follows.

BRIEF DESCRIPTION OF THE DRAWINGS

FIGS. 1 and 2 are two typical designs of an optical sensor. The carrier element, for example a plexiglass plate, is marked with the numeral 1; the excitation or fluorescence radiation, with the numeral 2 or 3.

Figure 1:
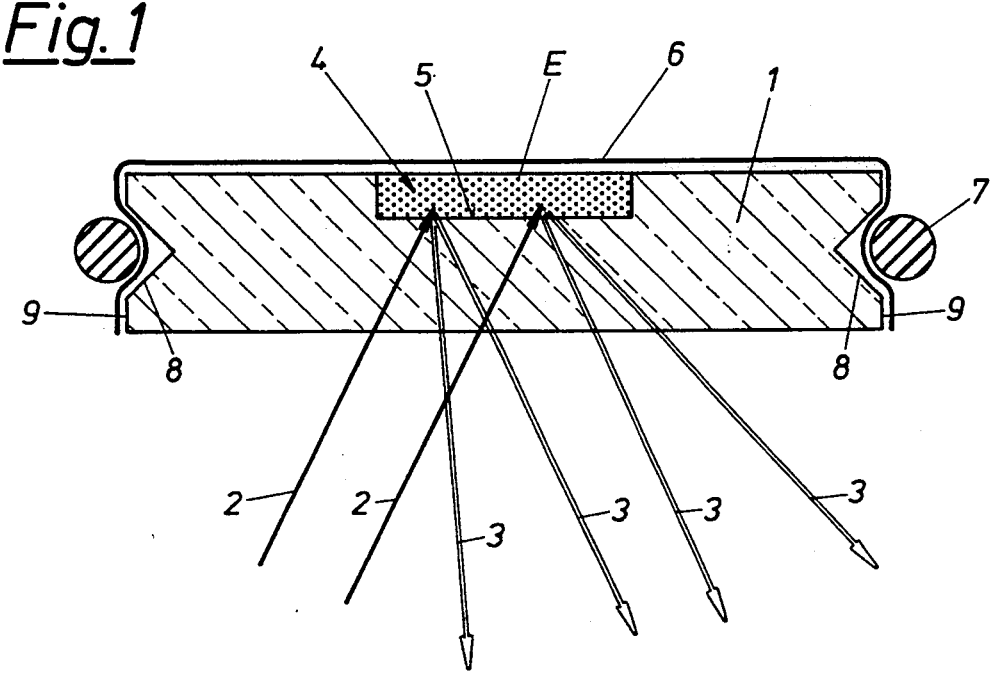
FIG. 1 is a cross sectional view through an optical sensor constructed according to a first embodiment of the present invention.

In the embodiment, shown in FIG. 1, the sensor layer 4 is located with the enzyme E in a sample-sided recess 5 of the carrier element 1 and is present as the enzyme solution or enzyme gel, which is mechanically immobilized by means of a membrane 6 that is impermeable to the enzyme. The membrane 6 is held securely on the side face 9 of the carrier element 1 in a groove 8 by means of an O-ring 7.

Figure 2:
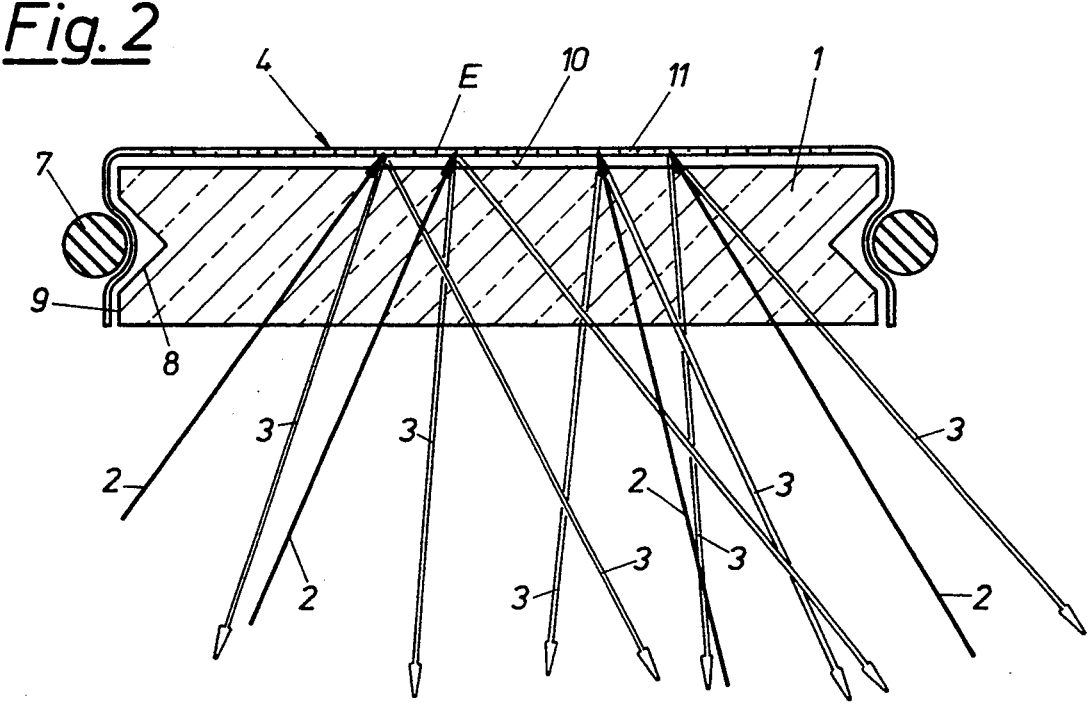
FIG. 2 is a cross sectional view through a second embodiment of optical sensor according to the present invention.

The optical sensor of FIG. 2 has on the side 10, facing the sample, an enzyme membrane 11, which forms the sensor layer 4 and which is fastened in the manner described in FIG. 1. The enzyme E is immobilized on or in the membrane 11.

Figure 3A:
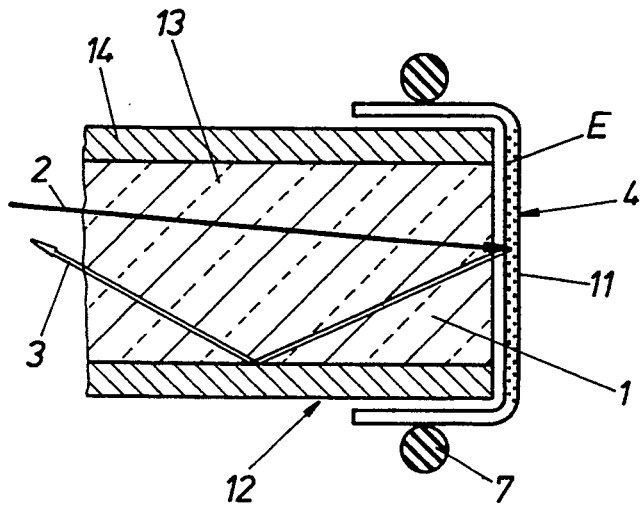
FIGS. 3a, 3b and 3c are cross sectional views through further optical sensor embodiments utilizing a light guide as the carrier element thereof, FIG. 4 schematically depicts a measuring apparatus using the inventive optical sensor.
Figure 3B:
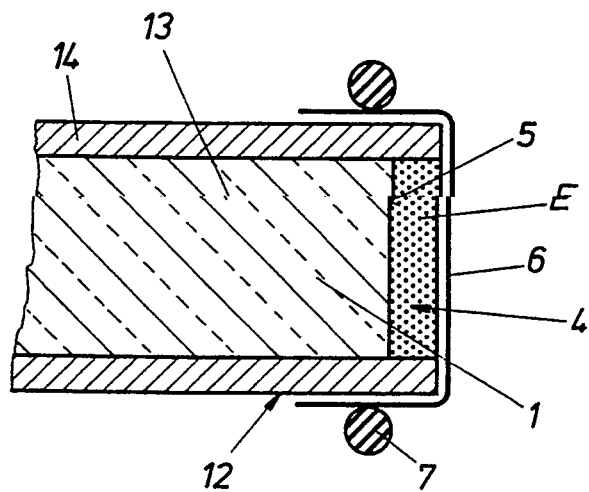
Figure 3C:
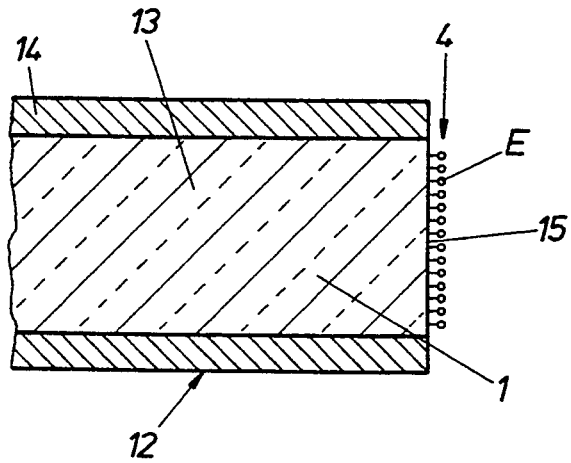

FIGS. 3a to c show typical possible arrangements in which the end 12 of a light guide is used as the carrier element 1. The core of the light guide is marked with the numeral 13 and its shell with the numeral 14. In FIG. 3a the enzyme is located on an enzyme membrane 11, which is fastened on the end 12 of the light guide with an O-ring 7. In FIG. 3b an enzyme solution or an enzyme gel is held securely on the end of the light guide in a recess 5 with a dialysis membrane 6 and an O-ring 7. Finally, the enzyme E in FIG. 3c is immobilized directly on the distal end 15 of the light guide.

In another conceivable embodiment the analytic signal can be obtained in that the enzyme is immobilized not on the distal end of the light guide but rather directly on the core 13 of the light guide, after the protective layer and the shell 14 have been removed in the end region of the light guide. In this case one measures with the aid of the so-called evanescent wave, i.e. the electric field vectors, which during the total reflection at the interface evanesces into the optically thinner phase. At that point the electric field vector can excite the fluorescence of the enzyme within the penetration depth. The fluorescence radiation couples into the optical waveguide and can be detected at its other end.

Figure 4:
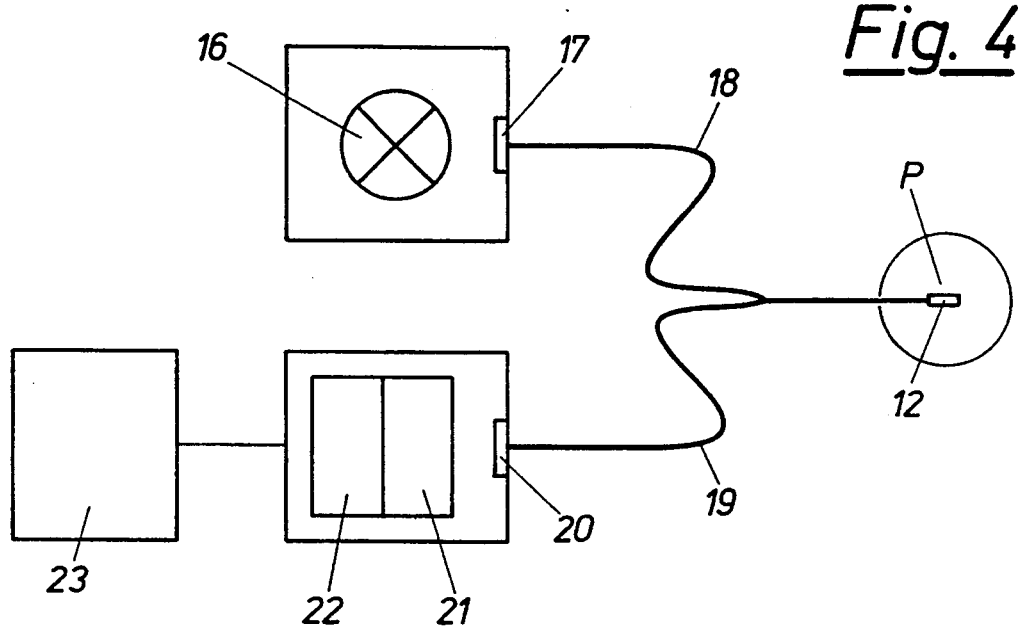

The measuring device, shown in FIG. 4, with a sensor of FIG. 3 at a test point P comprises a light source 16, which is in a position to supply light between 350 and 500 nm, an optical filter or monochromator 17, which narrows the excitation light to a narrow band range, a light guide arm 18, which guides the excitation light to the sensor at the end 12 of the two-armed light guide, and a second light guide arm 19, which guides the fluorescent light emitted by the enzyme over another monochromator 20 to a photo detector 21, an amplifying device 22 and an indicating element 23, which can also be coupled to an evaluation unit.

Suitable light sources are: halide lamps, xenon lamps (pulsed or continuous operation), light emitting diodes, laser and metal vapor lamps. Suitable optical filters are: interference filters, edge filters, prisms or grating monochromators. Preferably such light guides are used that are made of plastic or glass, since they have only a small risk of breaking, a feature that is very important for invasive methods. Not only fiber optical bundles but also single fibers can be used. Corresponding arrangements to separate irradiated light and fluorescent light have been known for a long time.

The radiation emitted by the sensor comprises the actual fluorescence radiation and a portion of scattered light, which is formed in the sensor zone by means of elastic or non-elastic scattering of the excitation radiation. To separate the scattered light, which is without any actual analytic information and is used at most as a reference signal, it is provided that said scattered light be separated with the aid of suitable filters. Such filters can be monochromators, dichroitic filters or high angle edge filters. Suitable light detectors are photo diodes, photo transistors or photo multipliers.

Figure 5:
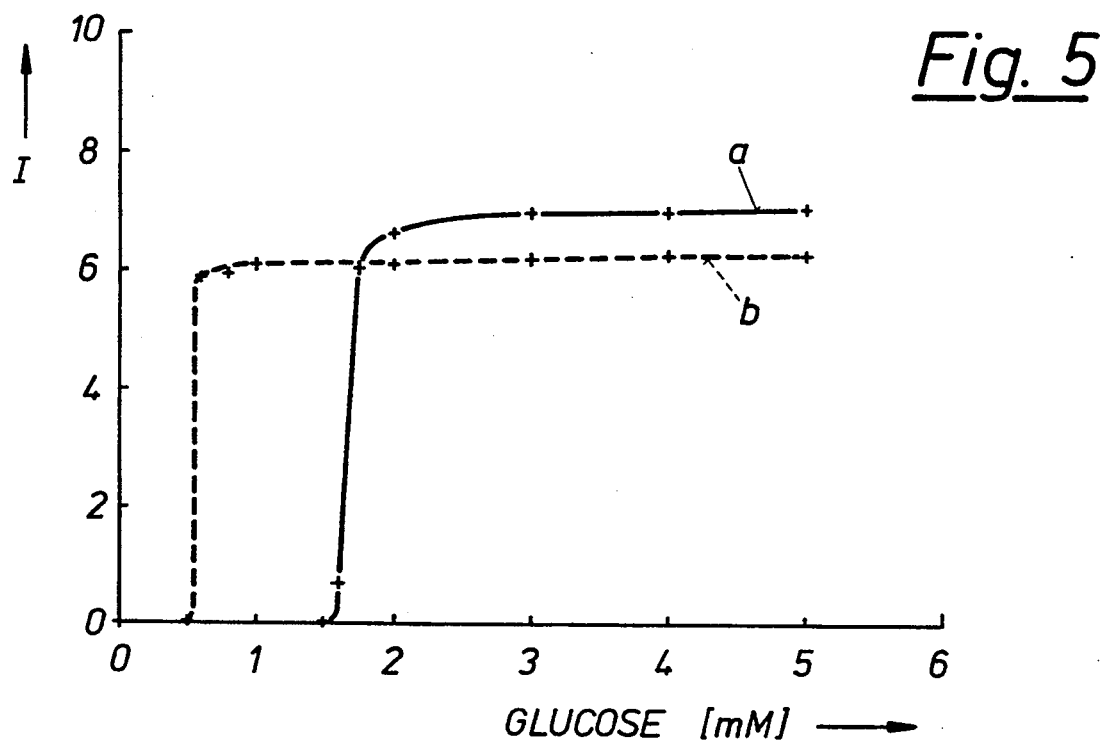
FIG. 5 is a graph of fluorescence intensity as a function of glucose concentration in a test solution, the fluorescence intensity being measured by the optical sensor of FIG. 1 (glucose oxidase with FAD)

FIG. 5 shows the intensity of fluorescence I as a function of the concentration of glucose in mM, measured with a sensor of FIG. 1. The flow was measured at pH=7 and 22.5° C. The dependence on the concentration of oxygen is shown by means of the two curves marked with the letters a and b, wherein the test solution is saturated with air at a and saturated with a mixture of $O_2$ and $N_2$ with 7.88% $O_2$ at b.

Figure 6:
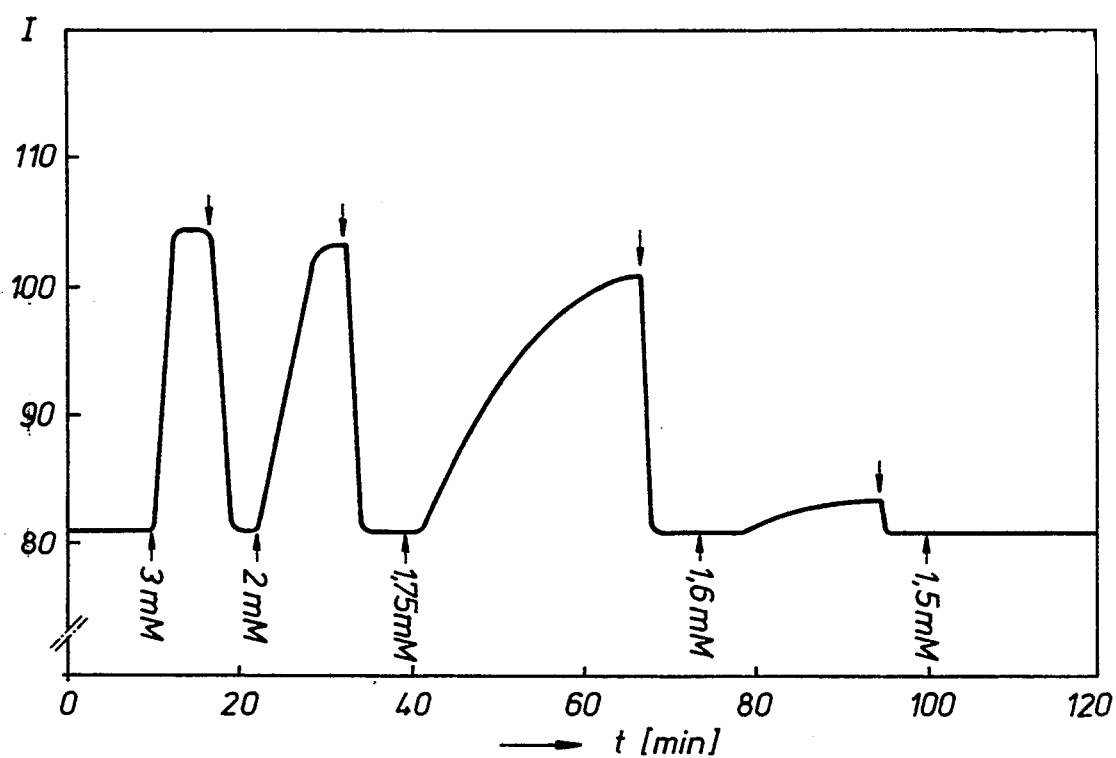
FIG. 6 is a graph of a typical response curve of a glucose sensor of FIG. 1 (glucose oxidase) for different concentrations of glucose in a flow.

FIG. 6 shows the typical response curve of a glucose sensor with glucose oxidase dissolved (configuration of FIG. 1) for different concentrations of glucose in the flow. The measurements were conducted at pH=7, temperature of 22.5° C. and air saturation.

Figure 7:
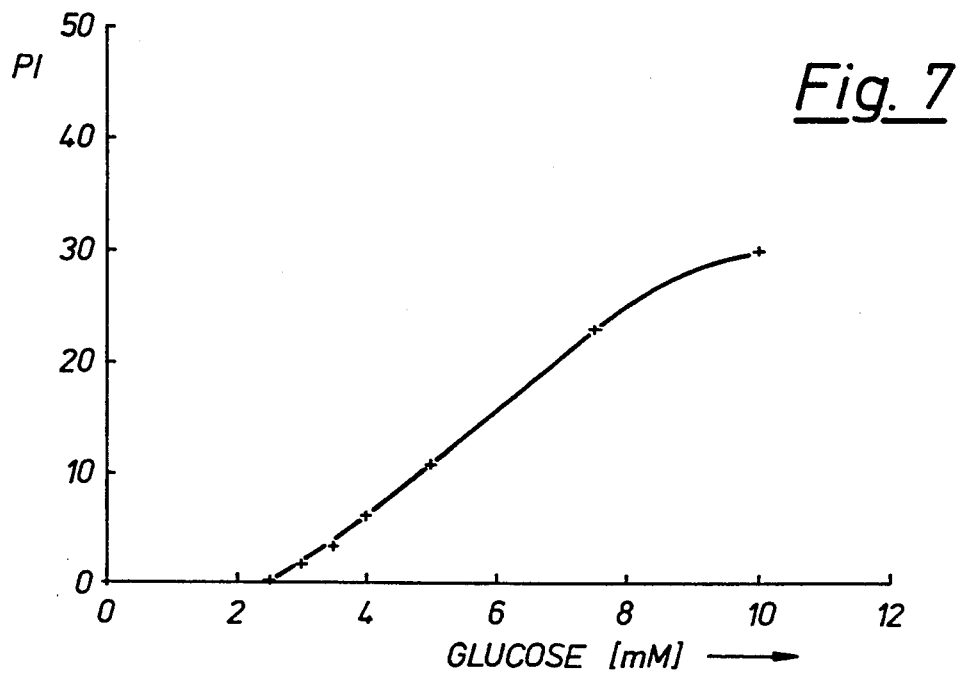
FIG. 7 is a graph of peak integral PI of a glucose sensor (FIG. 1) as a function of glucose concentration in a test solution passing through a flow cell.

FIG. 7 shows the peak integral PI of a glucose sensor as a function of the glucose concentration in mM, wherein the test solutions were pumped through the flow cell at 65 s. A configuration according to FIG. 1 was chosen as the measuring arrangement. The measurement was conducted at pH=7, 22.5° C. and air saturation.

From the above the conclusion can be drawn that the distinction between the optical biosensor of the invention and previous optical biosensors lies in the following points:

1) It permits a direct determination of the measurable variables, since no additional indicators have to be added to the sensor layer and thus no transducer element is necessary.

2) In contrast to many known optical biosensors there is only a single reaction chamber so that there is no need for mass transport from the indicator chamber to the reaction chamber.

3) No species that is formed by means of chemical reaction first or is consumed is measured, but rather the enzyme itself is measured.

4) In contrast to the sensors based on NADH, the sensor responds in a completely reversible manner and is compatible with the plastic light guides required in bio medicine due to the long-wave excitation and emission.

We claim:

1. A method for the continuous and reversible determination of the concentration of an enzyme substrate in a specimen, comprising the steps of:

(a) contacting said specimen containing said enzyme substrate with an enzyme specific for said substrate, selected from the group consisting of oxidases and oxygenases, to which a flavin coenzyme selected from the group consisting of flavin mononucleotide and flavin adenine dinucleotide is bonded, said flavin coenzyme converting to a reduced form by said enzyme substrate and to an oxidized form by molecular oxygen dissolved in said specimen, (b) measuring a change in intrinsic fluorescence of said flavin coenzyme under fluorescent excitation resulting from reduction of said flavin coenzyme occurring in step (a), and (c) determining the concentration of enzyme substrate in said specimen from the change in intrinsic fluorescence measured in step (b).

2. A method according to claim 1, including, prior to step (a), a step of adding molecular oxygen of a known concentration to said specimen to shift a region of response function in which small variations in concentration of enzyme substrate results in large changes in fluorescence intensity to a pre-set range of concentration.

3. A method according to claim 2, wherein an alcohol oxidase is used with a flavin adenine dinucleotide (FAD) for the determination of alcohol concentration.

4. A method according to claim 2, wherein a glutamic acid oxidase is used with a flavin coenzyme for the determination of glutamic acid concentration.

5. Method according to claim 2, wherein a glucose oxidase is used with a flavin adenine dinucleotide (FAD) for the determination of glucose concentration.

6. A method according to claim 1, wherein a glucose oxidase is used with a flavin adenine dinucleotide (FAD) for the determination of glucose concentration.

7. A method according to claim 1, wherein an alcohol oxidase is used with a flavin adenine dinucleotide (FAD) for the determination of alcohol concentration.

8. A method according to claim 1, wherein a glutamic acid oxidase is used with a flavin coenzyme for the determination of glutamic acid concentration.

* * * * *